US00PP22656P2

(12) United States Plant Patent
Smith

(10) Patent No.: US PP22,656 P2
(45) Date of Patent: Apr. 17, 2012

(54) *CHRYSANTHEMUM* PLANT NAMED 'SYNAZY URCORAL'

(50) Latin Name: *Chrysanthemum×morifolium*
Varietal Denomination: Synazy Urcoral

(75) Inventor: Mark A. Smith, Alva, FL (US)

(73) Assignee: Syngenta Crop Protection AG, Basel (CH)

( * ) Notice: Subject to any disclaimer, the term of this patent is extended or adjusted under 35 U.S.C. 154(b) by 31 days.

(21) Appl. No.: 12/925,315

(22) Filed: Oct. 19, 2010

(51) Int. Cl.
*A01H 5/00* (2006.01)

(52) U.S. Cl. ..... Plt./287

(58) Field of Classification Search ..... Plt./287, Plt./290
See application file for complete search history.

*Primary Examiner* — June Hwu
(74) *Attorney, Agent, or Firm* — S. Matthew Edwards

(57) ABSTRACT

A new *Chrysanthemum* plant named 'Synazy Urcoral' particularly distinguished by the average sized flowers with bold greyed-purple colored ray florets, dark yellow-green foliage, compact sphere-shaped plant habit and a natural season flowering about mid-September.

1 Drawing Sheet

Latin name of the genus and species of the plant claimed: *Chrysanthemum×morifolium.*

Varietal denomination: 'Synazy Urcoral'.

BACKGROUND OF THE NEW PLANT

The present invention comprises a new *Chrysanthemum*, botanically known as *Chrysanthemum×morifolium*, and hereinafter referred to by the variety name 'Synazy Urcoral'.

'Synazy Urcoral' is a product of a planned breeding program. The new cultivar has average sized flowers with greyed-purple colored ray florets, dark yellow-green foliage, compact sphere-shaped plant habit and a natural season flowering about mid-September.

'Synazy Urcoral' originates as a natural whole plant mutation of an unpatented, proprietary plant designated '00-M389EA'. 'Synazy Urcoral' was discovered outdoor in a large quantity trial format and selected by the inventor as a single flowering plant within a population of the parent cultivar in a controlled breeding program in Alva, Fla. in November 2007. The parent cultivar '00-M389EA' has lighter coral/orange ray floret color, larger plant habit, and slower flowering response time.

The first act of asexual reproduction of 'Synazy Urcoral' was accomplished when vegetative cuttings were propagated from the initial selection in December 2007 in a controlled environment in Alva, Fla.

BRIEF SUMMARY OF INVENTION

Horticultural examination of plants grown from cuttings of the plant initiated in December 2007, and continuing thereafter, has demonstrated that the combination of characteristics as herein disclosed for 'Synazy Urcoral' are firmly fixed and are retained through successive generations of asexual reproduction.

'Synazy Urcoral' has not been observed under all possible environmental conditions. The phenotype may vary significantly with variations in environment such as temperature, light intensity and day length.

A Plant Breeder's Right for this cultivar was applied for in Canada on Oct. 30, 2009 (09-6760). 'Synazy Urcoral' has not been made publicly available more than one year prior to the filing of this application.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'Synazy Urcoral' with colors being as true as possible with an illustration of this type.

The photographic drawing shows a flowering potted plant of the new variety and a close-up of the flowers.

DETAILED BOTANICAL DESCRIPTION

The plant descriptions and measurements were taken in Gilroy, Calif. in May 2010 under natural light. These plants were about 10 weeks old. The aforementioned photographs were taken in Gilroy, Calif. in late October 2009 outdoors. These plants were approximately 12 weeks of age.

Color references are made to The Royal Horticultural Society Colour Chart (R.H.S.) 2001.

TABLE 1

DIFFERENCES BETWEEN THE NEW VARIETY 'SYNAZY URCORAL' AND A SIMILAR VARIETY: 'FESTIVE YOURSULA' (U.S. Plant Pat. No. 15,324)

| | 'Synazy Urcoral' | 'Festive Yoursula' |
|---|---|---|
| Ray floret color: | More greyed purple | More deep coral |
| Plant habit size: | Smaller | Somewhat larger |
| Flowering response: | A couple days faster | A couple days slower |

Plant:

*Form, growth and habit.*—Herbaceous decorative garden type; stems upright and outwardly spreading, freely branching, strong and moderately vigorous growth habit.

*Plant height.*—10-14 cm.
*Plant height (inflorescence included).*—13-18 cm.
*Plant width.*—20-25 cm.
*Garden performance and tolerance to weather.*—Very good.

Roots:
*Number of days to initiate roots.*—About 4 days at about 22 degrees C.
*Number of days to produce a rooted cutting.*—10-12 days at 22 degrees C.
*Type.*—Fine, fibrous, free branching.
*Color.*—RHS N155B but whiter.

Foliage:
*Arrangement.*—Alternate, simple.
*Immature, leaf color, upper surface.*—Closest to RHS 137A.
*Lower surface.*—Closest to RHS 138A.
*Mature, leaf color, upper surface.*—Closest to RHS 137A but a little darker.
*Lower surface.*—Closest to RHS 138A but a little darker.
*Length.*—3.1-3.7 cm.
*Width.*—3.2-3.6 cm.
*Shape.*—Ovate.
*Base shape.*—Attenuate.
*Apex shape.*—Mucronulate.
*Margin.*—Palmately; irregularly lobed; sometimes irregularly serrate.
*Texture, upper surface.*—Bifid T-shaped hairs.
*Lower surface.*—Bifid T-shaped hairs.
*Color of veins, upper surface.*—RHS 144A.
*Color of veins, lower surface.*—RHS 144A.
*Petiole color.*—RHS 144A.
*Length.*—1.1-1.4 cm.
*Diameter.*—0.25-0.30 cm.
*Texture.*—Bifid T-shaped hairs.

Stem:
*Quantity of main branches per plant.*—About 10-12.
*Color of stem.*—RHS 146A.
*Length of stem.*—6-7 cm.
*Diameter.*—0.4 cm.
*Length of internodes.*—0.4-0.5 cm.
*Texture.*—Bifid T-shaped hairs.
*Color of peduncle.*—RHS 146A.
*Length of peduncle.*—4.5-7.0 cm.
*Peduncle diameter.*—0.15-0.2 cm.
*Texture.*—Bifid T-shaped hairs.

Inflorescence:
*Type.*—Compositae type, solitary inflorescences (decorative-type) borne terminally above foliage, ray florets arranged acropetally on a capitulum.
*Natural season flowering.*—About mid-September.
*Quantity of inflorescences per plant.*—About 32, plus about 12 buds.
*Lastingness of individual blooms on the plant.*—About 3-4 weeks.
*Fragrance.*—Slightly spicy.

Bud (just when opening/showing color):
*Color.*—RHS 185B.
*Length.*—0.7-1.0 cm.
*Width.*—0.9-1.0 cm.
*Shape.*—Oblate.

Immature inflorescence:
*Diameter.*—2.5-3.0 cm.
*Color of ray florets, upper surface.*—RHS 185A.
*Lower surface.*—Closest to RHS 185B.

Mature inflorescence:
*Diameter.*—4.0 cm.
*Depth.*—1.7 cm.
*Total diameter of 'disc'.*—0.5 cm.
*Receptacle height.*—0.4 cm.
*Receptacle diameter.*—0.5 cm.

Ray florets:
*Average quantity of florets.*—About 150 in numerous whorls.
*Color of florets, upper surface.*—RHS 185A quickly becoming closest to RHS 185B and maturing closest to RHS 185C.
*Lower surface.*—Closest to RHS 185B to RHS 185C.
*Length.*—1.5-1.9 cm.
*Width.*—0.5-0.6 cm.
*Shape.*—Oblong.
*Apex shape.*—Praemorse.
*Margin.*—Entire.
*Texture, upper surface.*—Papillose.
*Lower surface.*—Papillose.

Disc florets:
*Average quantity of florets.*—About 30.
*Color of florets.*—RHS 15A with RHS 1C basally and RHS 45A apex.
*Length.*—0.4 cm.
*Width.*—0.1 cm.
*Shape.*—Tubular, elongated.
*Apex shape.*—Acute, 5 pointed.

Phyllaries:
*Quantity.*—20-25.
*Color, upper surface.*—RHS 137A.
*Lower surface.*—RHS 137A to RHS 137B.
*Length.*—0.5-0.6 cm.
*Width.*—0.2-0.3 cm.
*Shape.*—Lanceolate.
*Apex shape.*—Acute.
*Based.*—Fused.
*Margins.*—Entire.
*Texture, upper surface.*—Glabrous.
*Lower surface.*—Bifid T-shaped hairs.

Reproductive organs:
*Pistil.*—1.
*Found on both florets.*—Yes.
*Length.*—0.25 cm.
*Style color.*—RHS 1C.
*Style length.*—0.2 cm.
*Stigma color.*—RHS 7A.
*Stigma shape.*—Bi-parted.
*Ovary color.*—Not observed.
*Stamens.*—1.
*Found on disc florets only.*—Yes.
*Color of filaments.*—RHS 1C.
*Length filaments.*—0.3 cm.
*Anther color.*—RHS 13A.
*Anther length.*—0.15 cm.
*Anther shape.*—Oblong.
*Color of pollen.*—RHS 13A.
*Pollen amount.*—Abundant.
*Fertility/seed set.*—Has not been observed on this hybrid.

Disease/pest resistance: Disease/pest resistance has not been observed on this hybrid.

What is claimed is:

1. A new and distinct variety of *Chrysanthemum* plant named 'Synazy Urcoral' substantially as illustrated and described herein.

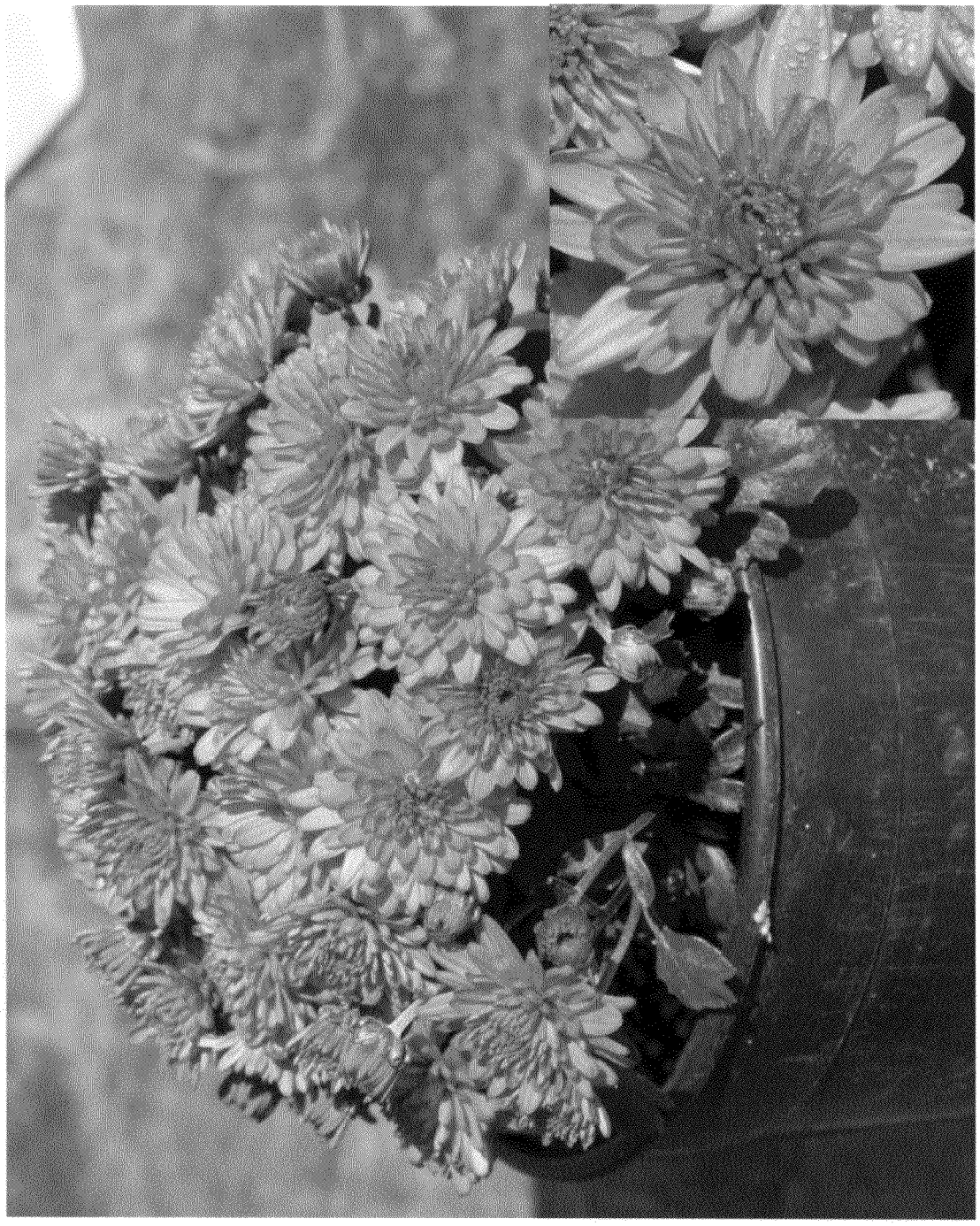

* * * * *